United States Patent [19]

Blitstein-Willinger

[11] Patent Number: 5,506,265
[45] Date of Patent: Apr. 9, 1996

[54] PROSTACYCLIN AND CARBACYCLIN DERIVATIVES AS AGENTS FOR THE TREATMENT OF MULTIPLE SCLEROSIS

[75] Inventor: Eveline Blitstein-Willinger, Berlin, Germany

[73] Assignee: Schering Aktiengesellschaft, Berlin, Germany

[21] Appl. No.: 284,527

[22] PCT Filed: Jan. 9, 1993

[86] PCT No.: PCT/DE93/00013

§ 371 Date: Dec. 6, 1994

§ 102(e) Date: Dec. 6, 1994

[87] PCT Pub. No.: WO93/14761

PCT Pub. Date: Aug. 5, 1993

[30] Foreign Application Priority Data

Jan. 28, 1992 [DE] Germany .......................... 42 02 665.2

[51] Int. Cl.[6] .................. A61K 31/19; C07C 321/00; C07C 69/76
[52] U.S. Cl. ................. 514/573; 560/56; 560/10
[58] Field of Search .............. 514/573; 560/56, 560/10

[56] References Cited

U.S. PATENT DOCUMENTS 4,788,319  11/1988  Hazato et al. ........................ 560/11

OTHER PUBLICATIONS

Sharief et al., "Association Between Tumor Necrosis Factor–alpha and Disease Progression in Patients with Multiple Sclerosis," *The New England Journal of Medicine*, vol. 325, No. 7, Aug. 15, 1991, pp. 467–472.

R. Benvenuto et al., "Increased Synthesis of Tumor Necrosis Factor by Cerebrospinal Fluid Derived T–Cell Clones from Patients with Multiple Sclerosis," *J. Neurol.*, vol. 237, No. SUP1, 1990, p. 83.

Sliwa et al., "Prevention of Murine Cerebral Malaria by a Stable Prostacyclin Analog," *Infection and Immunity*, vol. 59, No. 10, Oct. 1991, pp. 3846–3848.

Kirby et al., "Prostacyclin Increases Cyclic–Nucleotide Responsiveness of Lymphocytes from Patients with Systemic Sclerosis," *The Lancet*, vol. 2, No. 8192, Aug. 30, 1980, pp. 453–454.

*Primary Examiner*—Theodore J. Criares
*Attorney, Agent, or Firm*—Millen, White, Zelano, & Branigan

[57] ABSTRACT

This invention relates to the use of prostacyclin and carbacyclin derivatives for the production of an agent for the treatment of multiple sclerosis.

7 Claims, No Drawings

PROSTACYCLIN AND CARBACYCLIN DERIVATIVES AS AGENTS FOR THE TREATMENT OF MULTIPLE SCLEROSIS

This application is filed under 35 USC 371 of PCT/DE93/00013 filed Jan. 9, 1995.

This invention relates to agents for the treatment of multiple sclerosis, a primary inflammatory disease of the central nervous system with localized demyelination.

The agents contain prostacyclin and carbacyclin derivatives and common auxiliary agents and vehicles. The invention also relates to the use of these prostacyclin and carbacyclin derivatives for the production of the above-mentioned agents.

The pharmacological effects of prostacyclin and carbacyclin derivatives, which can be mainly attributed to their cardiovascular and thrombocyte aggregation-inhibiting action, are already known from EP 11591, EP 55208, EP 99538, EP 119949 and EP 84856. It has been found that agents containing prostacyclin and carbacyclin derivatives are suitable for the treatment of multiple sclerosis which is accompanied by various neurological symptoms with a primarily intermittent course, partial remission but chronic progression.

The salts of these prostacyclin and carbacyclin derivatives with physiologically well tolerated bases and their β-cyclodextrin clathrates can also be used for the treatment of the above-mentioned disease.

Multiple sclerosis always has a chronic, recurrent course. The association with immunological defects can be attributed to both the T cell level (W. W. Tourtellotte et al., J. Neuroimmunol 1988; 20:217–27) and the B cell level (B. H. Waksman et al.; Proc. Soc. Exp. Biol. Med. 1984, 175:282–94). In the active foci in the brain, in most cases perivascularly located, dense cellular infiltrates consisting of lymphocytes and macrophages, with at the same time selective demyelination (later gliosis-like scarring) have been described histologically (S. L. Hauser et al.; Ann Neurol 1968, 19:578–87).

Both cell types secrete a tumor necrosis factor (TNFα), a cytokine which is an important mediator in primary inflammatory diseases including those in the central nervous system area (M. M. Mustafa et al.; Pediatr. Infect Dis. J. 1989; 8:907–7; M. M. Mustafa et al.; J. Pediatr. 1989; 115:208–13; M. Mintz et al.; Am. J. Dis. Child 1989; 143:771–4). K. W. Selmaj et al.; Ann. Neurol. 1988; 23:339–46 report that TNFα can induce a selective cytotoxicity with respect to oligodendrocytes and the myelin sheath "in vitro". A clinical study of 32 patients (M. K. Sharif et al.; New Engl. J. of Med. Vol. 325, 7 476–470) shows that an elevated TNF synthesis takes place intrathecally in patients with M.S. and that the TNFα level of the cerebrospinal liquor is correlated with the severity and progression of the disease.

Surprisingly, it has now been found that the above-mentioned prostacyclin and carbacyclin derivatives, as a function of dosage, inhibit the synthesis of TNF at the TNF-messenger RNA stage.

Prostacyclins and carbacyclins inhibit TNF synthesis on the mRNA level. Thus they are preferable as therapeutic agents to monoclonal antibodies, which are aimed only TNF that is already present. The monoclonal antibodies act only on already secreted TNF. The TNF-αTNF immunocomplexes that are formed must, in turn, be catabolized, which can lead to clinical complications. In addition, the above-mentioned prostacyclins and carbacyclins are used prophylactically in cases involving these diseases; this cannot be done with monoclonal antibodies.

The advantage of the new agents over $PGE_2$ lies in the marked reduction of side-effects. PGE 2 causes, e.g., itself fever, leads to elevated constriction of the smooth muscles and, in addition, has an abortive action. By contrast, the new agents exert a vessel-protective and antiedematous effect.

Iloprost, Cicaprost, Eptaloprost, Beraprost, and Ciprosten have proved to be especially suitable prostacyclin and carbacyclin derivatives.

Inorganic and organic bases are suitable for forming salts with the free acids as they are known to the specialist for the formation of physiologically well-tolerated salts. Alkali hydroxides, such as sodium hydroxide and potassium hydroxide, alkaline-earth hydroxides, such as calcium hydroxide, ammonia, amines, such as ethanol amine, diethanol amine, triethanol amine, N-methylglycamine, morpholine, tris-(hydroxymethyl)-methyl amine, etc. can be mentioned as examples. β-cyclodextrinclathrate formation takes place as described in EP 25 94 68.

The production of the above-mentioned prostacyclin and carbacyclin derivatives is described in detail in EP 11591, 55208, 119949, 99538, and 84856.

The following pharmacological properties are described in these patents for the prostacyclin and carbacyclin derivatives: reduction of peripheral arterial and coronary vascular resistance, inhibition of the thrombocyte aggregation and dissolution of platelet thrombi, myocardial cytoprotection; reduction of the systemic blood pressure without reducing cardiac output and coronary blood circulation at the same time; treatment of stroke, prophylaxis and treatment of coronary heart diseases, coronary thrombosis, myocardial infarction, peripheral arterial disease, arteriosclerosis and thrombosis, treatment of shock, inhibition of bronchoconstriction, inhibition of gastric acid secretion and cytoprotection of the gastrointestinal mucous membrane; antiallergic properties, reduction of pulmonary vascular resistance and pulmonary blood pressure, promotion of renal circulation, use as substitutes for heparin or as an adjuvant in dialysis or hemofiltration, preservation of dried blood plasma, especially blood platelet preservation, inhibition of labor pains, treatment of toxicosis in pregnancy, increase of cerebral circulation, and antiproliferation.

The pharmacological properties which are new for the above-mentioned prostacyclin and carbacyclin derivatives have not been described and also have no direct connection with the effects described in the EP patents.

The dosage of the compounds is 1–1500 μg/kg/day when administered to human patients. The unit dosage for the pharmaceutically acceptable vehicle is 0.1–100 mg.

The administration of these agents by i.v. as a continuous infusion in usual aqueous solvents, e.g., 0.9% NaCl solution, is preferably done at dosages of between 0.1 ng/kg/min and 0.1 μg/kg/min.

The active ingredients according to the invention should be used in connection with auxiliary agents that are common and known in galenicals for, e.g., the production of cerebrally active agents.

The invention also relates to a process for the production of the agents according to the invention, characterized in that, in a way known in the art, the compounds that are effective in the case of cerebral complications are combined with auxiliary agents and vehicles known in the art into a galenical formulation.

EXAMPLE 1

In vitro tests show that, as a function of dosage, Iloprost inhibits the TNF production of NMRI-mouse peritoneal macrophages that is induced by 50 µg/ml of lipopolysaccharide (LPS) (FIGS. 1, 2).

Intraperitoneal injection of 2% starch solution is used to induce local sterile inflammations in NMRI mice. After 3–5 days the animals are sacrificed and the macrophages obtained. The nonadhering cells are separated.

To activate the macrophages, LPS in concentrations of 1.5 µg and 50 µg/ml is used.

As an TNF assay the TNF-sensitive cell line WEHI 164 (commercially available) is used. The extent of the cell lysis of WEHI 164 is proportional to the amount of TNF present. In 96 cup-type flat-bottom microtiter plates, the culture supernatants and sera are titrated off in a dilution series. A titration series with TMU-TNF is used as a standard.

The number of surviving cells is determined based on the calorimetric MTT test. The calculation is performed by comparison with the standard titration series of TMU-TNF by means of probit analysis.

The test makes it possible to determine up to 0.5 U/ml TNF. $TNF\alpha$ and $TNF\beta$ are distinguished by adding an anti-TNF antiserum.

EXAMPLE 2

The serum TNF levels of untreated mice and of mice treated with Iloprost are studied.

Iloprost significantly inhibits the TNF levels in the serum even 4 days after the last injection.

EXAMPLE 3

Iloprost (1.000–0.01 ng/ml) inhibits the TNF production of human peripheral macrophages induced by LPS.

This inhibition can be achieved even when Iloprost is added 3 hours after LPS administration.

I claim:

1. A method of treating multiple sclerosis in a patient in need of such treatment comprising administering to the patient an effective amount of a prostacyclin or a carbacyclin compound.
2. A method of claim 1, wherein said compound is iloprost, cicaprost, eptaloprost, beraprost or ciprosten.
3. A method of claim 1, wherein said compound is iloprost.
4. A method of claim 1, wherein said compound is administered as a salt or cyclodextrin-clathrate.
5. A method of claim 2, wherein said compound is administered as a salt or cyclodextrin-clathrate.
6. A method of claim 3, wherein said compound is administered as a salt or cyclodextrin-clathrate.
7. A method of claim 1, wherein the compound is administered by continuous infusion of 0.1 ng/kg/min to 0.1 µg/kg/min.

* * * * *